US009664623B2

(12) United States Patent
Lambert et al.

(10) Patent No.: US 9,664,623 B2
(45) Date of Patent: May 30, 2017

(54) METHOD FOR DETECTING THE TRANSITION OF PRODUCTS IN A CONDUIT

(75) Inventors: Didier Lambert, Saint Mitre les Remparts (FR); Bernard Ribero, Marseilles (FR); Claude Saint-Martin, Pelissanne (FR); Miguel Sanchez, Lavera (FR)

(73) Assignee: TOPNIR SYSTEMS SAS, Aix en Provence (FR)

( * ) Notice: Subject to any disclaimer, the term of this patent is extended or adjusted under 35 U.S.C. 154(b) by 194 days.

(21) Appl. No.: 14/377,324

(22) PCT Filed: Feb. 7, 2012

(86) PCT No.: PCT/EP2012/052041
§ 371 (c)(1),
(2), (4) Date: Nov. 14, 2014

(87) PCT Pub. No.: WO2012/089851
PCT Pub. Date: Jul. 5, 2012

(65) Prior Publication Data
US 2015/0098083 A1   Apr. 9, 2015

(51) Int. Cl.
| G01N 21/85 | (2006.01) |
| G01N 21/31 | (2006.01) |
| G01N 21/359 | (2014.01) |
| G01N 21/84 | (2006.01) |
| G01N 21/3577 | (2014.01) |

(52) U.S. Cl.
CPC ............. *G01N 21/85* (2013.01); *G01N 21/31* (2013.01); *G01N 21/359* (2013.01); *G01N 21/84* (2013.01); *G01N 21/3577* (2013.01); *G01N 2021/8411* (2013.01); *G01N 2201/088* (2013.01)

(58) Field of Classification Search
CPC .. G01N 21/85; G01N 21/84; G01N 2201/088; G01N 2021/8411
USPC ...................................... 702/28, 30
See application file for complete search history.

(56) References Cited

U.S. PATENT DOCUMENTS

| 5,139,334 A * | 8/1992 | Clarke | .................. G01N 21/65 356/301 |
| 5,349,188 A * | 9/1994 | Maggard | .............. G01N 21/359 250/339.12 |
| 5,404,015 A | 4/1995 | Chimenti et al. | |
| 5,712,481 A | 1/1998 | Welch et al. | |

(Continued)

FOREIGN PATENT DOCUMENTS

| ES | 2 186 549 | 5/2003 |
| FR | 2 906 034 | 3/2008 |

OTHER PUBLICATIONS

International Search Report for PCT/EP2012/052041 dated May 10, 2012.

(Continued)

*Primary Examiner* — Sang Nguyen
(74) *Attorney, Agent, or Firm* — Stephen J. Weyer, Esq.; Stites & Harbison, PLLC.

(57) ABSTRACT

This invention relates to a method of detecting the transition, between a first compound and a second compound, of a product, which may contain such a first compound and/or such a second compound, and flowing inside a conduit for conveying this product.

15 Claims, 2 Drawing Sheets

(56) References Cited

U.S. PATENT DOCUMENTS

| | | | |
|---|---|---|---|
| 5,763,883 A * | 6/1998 | Descales | G01N 33/2829 |
| | | | 250/339.09 |
| 8,030,618 B2 * | 10/2011 | Okamoto | B29C 43/003 |
| | | | 250/370.09 |
| 8,847,163 B2 * | 9/2014 | Foster | G01J 3/42 |
| | | | 250/339.12 |
| 9,018,584 B2 * | 4/2015 | Chernokalskaya | |
| | | | G01N 21/3563 |
| | | | 250/339.07 |
| 9,185,200 B2 * | 11/2015 | Cunningham | G01J 3/28 |
| 9,252,560 B2 * | 2/2016 | Fermann | G01N 21/31 |
| 9,341,515 B2 * | 5/2016 | Schulte | G01J 3/0289 |
| 2004/0033617 A1 | 2/2004 | Sonbul | |
| 2006/0053005 A1 * | 3/2006 | Gulati | G06F 19/20 |
| | | | 704/226 |
| 2006/0283931 A1 * | 12/2006 | Polli | G01N 21/3581 |
| | | | 235/375 |
| 2007/0143037 A1 * | 6/2007 | Lundstedt | G01N 21/274 |
| | | | 702/30 |
| 2008/0311672 A1 * | 12/2008 | Dasgupta | G01N 1/4005 |
| | | | 436/161 |
| 2010/0211329 A1 | 8/2010 | Farquharson et al. | |

OTHER PUBLICATIONS

Written Opinion of the International Searching Authority for PCT/EP2012/052041 dated May 10, 2012.

* cited by examiner

METHOD FOR DETECTING THE TRANSITION OF PRODUCTS IN A CONDUIT

FIELD OF THE INVENTION

This invention relates to a method characterizing a product, flowing within a conduit for conveying this product, and which may contain a first compound and/or a second compound.

More particularly, said characterization method comprises a method for the detection of the transition of such a product between a first compound and a second compound. This characterization process may again consist of a method of determining the composition of such a product.

This invention, again, relates to a device for characterization of such product.

This invention relates to the field of characterization of products flowing inside a conduit for conveyance of such a product and that comprises an installation, chiefly of the industrial type. In particular, this invention will find its application when one needs to detect, within such a conduit for conveyance, a transition between a product consisting of a first compound and a product consisting of a second compound.

BACKGROUND OF THE INVENTION

Methods are known already which are used to characterize such a product, and they consist of, in space and time, the removal of, from the inside of such a conduit for conveyance, a set quantity of product to provide the analysis outside of this conduit.

Consequently, implementing such a method would require a special arrangement of the conduit making it possible to perform said sampling (bypass conduit, valves, opening . . . ), to access the product sampled or to be sampled and/or to retrieve the product sampled in order to analyze it, which, based on the implementation and/or the environment of such a conduit, this can be problematic.

Moreover, between the time when a sample is taken of the product and the moment when this product is analyzed, it takes a while for a transition to be started, or to be completed without having been detected. This results in uncertainty of the exact timing of this transition so that, to avoid loading or shipping a product containing an inappropriate compound, a significant amount of product is removed which may be considered for downgrading as it may contain inappropriate compound.

Another disadvantage is that the characterization of such a product is usually carried out based on at least one physical property of such a product. This product is then characterized by a physical quantity corresponding to such a physical property. Firstly, we observed that this type of characterization based on a physical property, does not always make it possible to discriminate adequately between a first compound and a second compound, let alone with respect to a mixture of these first and second compounds, which then prevents such characterization based on such a physical property and, secondly, it generally lacks accuracy which prevents an accurate characterization of this product and, for example, does not allow one to determine the transition accurately.

SUMMARY OF THE INVENTION

This invention aims to remedy the drawbacks of the Prior Art.

To this end, the invention relates to a method of characterizing a product flowing inside a conduit for conveyance of the product, and may contain a first compound and/or a second compound.

This characterization method is characterized in that:

an absorption spectrum was recorded for each sample from a first plurality of samples from the first pure compound as well as for each sample of a plurality of samples from the second pure compound;

from the absorption spectra identified through the samples from the first and second pure compounds, we are able to determine at least one spectral marker, common to the first compound and the second compound, thus discriminating the first and second compound, and consisting of a function of a plurality of absorbances from such a spectrum;

first, from the absorption spectra identified through the samples from the first and second pure compounds, at least one predetermined spectral marker is defined, a first spectral box consisting of a first spectral range delimited by the values of at least one such spectral marker determined and corresponding to the first pure compound and, secondly, a second spectral box constituted by a second spectral range delimited by the values of at least one such determined spectral marker and corresponding to the second pure compound;

inside the conduit for conveyance of the product, at least one absorption spectrum of the product flowing inside this conduit is identified;

For at least one such absorption spectrum identification for the product flowing inside the conduit, the value of at least one spectral marker is determined which corresponds to at least one predetermined spectral marker for the first and second pure compounds;

firstly, said product is characterized based on the first and second spectral boxes and, secondly, on the value of at least one determined spectral marker which corresponds to at least one absorption spectrum identification for the product.

Yet, this invention relates to a method of detecting the transition, between a first compound and a second compound, of a product, which may contain such a first compound and/or such a second compound, and which flows inside a conduit for conveying this product. This detection method is characterized in that it detects the transition of the product implementing the aforementioned method of characterization and wherein the characterization of the product consists of detecting such a transition of this product.

This invention also relates to a method for determining the composition of a product, flowing within a conduit for conveying this product, and which may contain a first compound and/or a second compound. This method is characterized in that it determines the composition of the product by implementing the aforementioned method of characterization and wherein the characterization of the product is to determine the composition of this.

Finally, the invention relates to a device to characterize this product flowing inside a conduit for conveyance of the product, and which may contain a first compound and/or a second compound, said device being designed specifically to implement the method described above. This device is characterized in that it comprises:

a database containing at least the absorption spectra of a plurality of samples from the first pure compound and of a plurality of samples from the second pure compound;

the means to determine at least one spectral marker, common to the first compound and to the second compound, discriminating thus discriminating the first and second compounds, and consisting of a function of a plurality of absorbances from such a spectrum;

means to define, firstly, a first spectral box constituted by a first spectral range delimited by the values of at least one such determined spectral marker and corresponding to the first pure compound and, secondly, a second spectral box constituted by a second spectral range delimited by the values of at least one such determined spectral marker and corresponding to the second pure compound, for at least one predetermined spectral marker;

means to identify, inside the conduit for conveyance of the product, at least one absorption spectrum of the product flowing inside this conduit;

means to determine the value of at least one spectral marker corresponding to at least one predetermined spectral marker for the first and second pure compounds, for at least one absorption spectrum identified for the product flowing inside the conduit.

means to characterize said product, based on, firstly, the first and second spectral boxes and, secondly, on the value of at least one determined spectral marker which corresponds to at least one absorption spectrum identification for the product.

The method in accordance with the invention consists in particular of identifying at least the absorption spectrum of a product, directly inside a conduit for conveyance.

In an advantageous manner, the identification of such a spectrum is, then, performed in situ and it reflects, at the time of this identification, the exact characteristics of the product of which said spectrum is recorded.

According to another advantage, the characterization of a product only requires, therefore, more sampling under conditions which are at times difficult, of a certain amount of product inside a conduit. The new method therefore makes it possible to facilitate such a characterization and it also offers the advantage of being nondestructive.

In an advantageous manner, a further orifice to introduce a spectrometer probe within the conduit for conveyance, implementation of this new method needs no particular arrangement for such a conduit for conveyance or facility comprising said conduit.

Moreover, this new method may be implemented at any point in the conduit for conveyance of the product, regardless of environmental constraints or accessibility to such conduit previously imposed by the need to sample the product according to the methods of the Prior Art. In particular, the identification of the spectra can then be performed sufficiently upstream from the end of the conduit for conveyance which then makes it possible to intervene at the level of this end, including changing the direction of product flow in time, in spite of the product flow rate within this conduit.

In addition, this new method consists of identifying at least one spectrum and processing such a spectrum instantly which makes it advantageously possible to characterize a product in real time, and thus immediately intervene on the delivery of the product, more particularly on the direction in which the product traveling. This advantageously makes it possible to maximize the quantity of non-degraded product during the transition thereof.

Another advantage is that, from the spectra observed for the pure compounds, one may determine at least one spectral marker that consists of a function of a plurality of relevant absorption spectra from a pure compound. This type of spectral marker then advantageously allows characterization of the first and second compounds as well as the product that should be optimally characterized, on the one hand, and with increased accuracy and, on the other hand, without using a characterization based solely on physical properties relating to the compounds as in the Prior Art.

Another advantage consists in that this method is able to be implemented by all types of product in movement on the inside of a conduit for conveyance.

Advantageously, this method may be implemented for any type of conduit for conveyance, including a feed line (more specifically, a feed pipe line at an industrial site), for transfer (especially a pipe line for the transfer of crude oil, both the intermediate and the finished product), or for loading or any other type of conveyor.

Finally, this method is advantageously suitable for being implemented in all industrial processes requiring characterization of products circulating in conduits for conveyance and finds a particularly appropriate application (but not exclusively) in refineries, in production units (distillation, conversion . . . ), in mixing (especially for fuel, lubricants, paints) or others.

Other purposes and advantages of this invention will appear in the description, given hereafter in reference to the embodiments which are given as non-restrictive indicative examples.

BRIEF DESCRIPTION OF THE DRAWINGS

The understanding of this description will be facilitated by reference to the attached drawing and wherein.

DETAILED DESCRIPTION OF THE INVENTION

Figure 1:
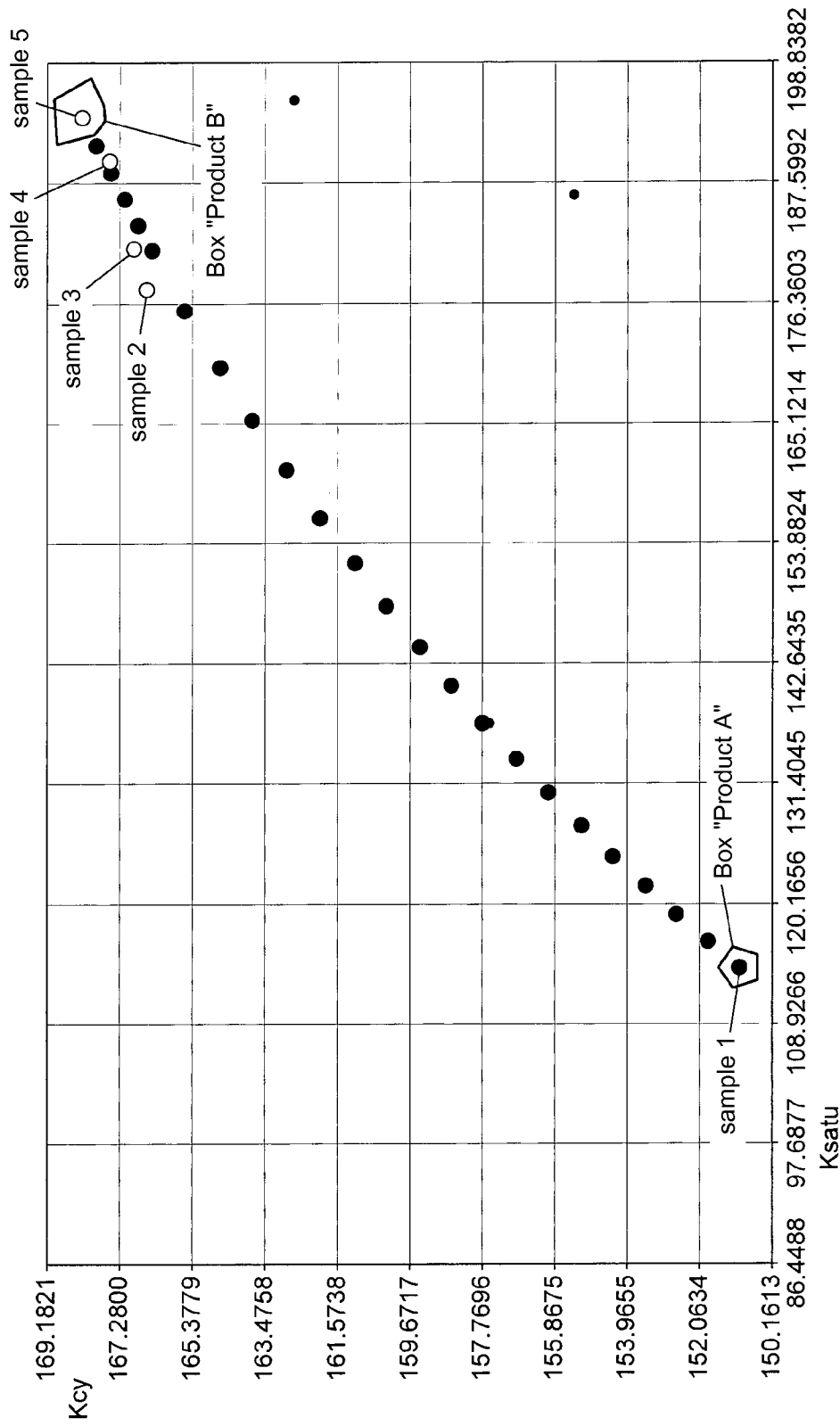
FIG. 1 is a graphic view of the characterization of a product consisting of detecting the transition between a product of a first compound and a second compound.

This invention relates to the field of characterization of products flowing inside a conduit for conveyance of such a product and that comprises an installation, chiefly of the industrial type.

This invention relates to a method characterizing a product, flowing within a conduit for conveying this product, and which may contain a first compound and/or a second compound.

This method of characterization consists of:

an absorption spectrum was identified for each sample from a first plurality of samples from the first pure compound as well as for each sample of a plurality of samples from the second pure compound;

from the absorption spectra identified through samples of the first and second pure compounds, we are able to determine at least one spectral marker, which is common to the first and second compounds, thus discriminating between the first and second compounds, (characteristic for each of these compounds), and consisting of a function of a plurality of absorbances from such a spectrum;

first, from the absorption spectra identified for the samples from the first and second pure compounds, we can define for at least one predetermined spectral marker a first spectral box constituted by a first spectral range delimited by the values of at least one such determined spectral marker and corresponding to the first pure compound and, secondly, a second spectral box constituted by a second spectral range delimited by the values of at least one such spectral marker determined and corresponding to the second pure compound;

inside the conduit for conveyance of the product, at least one absorption spectrum of the product flowing inside this conduit is identified;

using at least one such absorption spectrum identified for the product flowing inside the conduit we can determine the value of at least one predetermined spectral marker for the first and second pure compounds;

on one hand, said product is characterized based on first and second spectral boxes and, on the other hand, from the value of at least one spectral marker determined and corresponding to at least one absorption spectrum identified for the product.

One embodiment of this method consists of:

from the absorption spectra identified through samples of the first and second pure compounds, we are able to determine one spectral marker, which is common to the first and second compounds, thus discriminating between the first and second compounds, and consisting of a function of a plurality of absorbances from such a spectrum;

first, from the absorption spectra identified for the samples from the first and second pure compound, one predetermined spectral marker is defined, a first spectral box consists of a first range of values of the spectral marker determined and corresponding to the first pure compound and, secondly, a second spectral box consists of a second range of values of the spectral marker determined and corresponding to the second pure compound.

This particular embodiment consists of:

inside the conduit for conveyance of the product, at least one absorption spectrum of the product flowing inside this conduit is identified;

using at least one such absorption spectrum identified for the product flowing inside the conduit, we can determine the value of the spectral marker corresponding to the predetermined spectral marker for the first and second pure compounds;

on one hand, said product is characterized based on first and second spectral boxes and, on the other hand, from the value of at least one spectral marker determined and corresponding to at least one absorption spectrum identified for the product.

However, according to a preferred embodiment of the invention, this method of characterization consists of:

an absorption spectrum was identified for each sample from a first plurality of samples from the first pure compound as well as for each sample of a plurality of samples from the second pure compound;

from the absorption spectra identified through samples of the first and second pure compounds, we are able to determine two spectral markers, which is common to the first and second compounds, thus discriminating between the first and second compounds, and each consisting of a function of a plurality of absorbances from such a spectrum;

first, from the absorption spectra identified for the samples from the first and second pure compound, on one hand, a first spectral box is defined constituted by a first spectral range delimited by the values of these two spectral markers determined and corresponding to the first pure compound and, on the other hand, a second spectral box constituted by a second spectral range delimited by the values of these two spectral markers determined and corresponding to the second pure compound, for the two predetermined spectral markers and in a plane corresponding to these two spectral markers inside the conduit for conveyance of the product, at least one absorption spectrum of the product flowing inside this conduit is identified;

using at least one such absorption spectrum identified for the product flowing inside the conduit, we can determine the value of two spectral markers corresponding to the predetermined two spectral markers for the first and second pure compounds;

on one hand, said product is characterized based on first and second spectral boxes and, on the other hand, from the value of at least one spectral marker determined (preferably from the value of the two predetermined spectral markers) and corresponding to at least one absorption spectrum identified for the product.

On this matter, it should be noted that according to another particular embodiment of the invention, this characterization method may, again, consist of:

from the absorption spectra identified through samples of the first and second pure compounds, we are able to determine at least three spectral markers, which are common to the first and second compounds, thus discriminating between the first and second compounds, and each consisting of a function of a plurality of absorbances from such a spectrum;

first, from the absorption spectra identified for the samples from the first and second pure compound, on one hand, a first spectral box is defined constituted by a first spectral range delimited by the values of these spectral markers determined and corresponding to the first pure compound and, on the other hand, a second spectral box constituted by a second spectral range delimited by the values of these spectral markers determined and corresponding to the second pure compound, for at least the three predetermined spectral markers; and in a space corresponding to these spectral markers;

said product may be characterized based on, firstly, the first and second spectral boxes and, secondly, from the value of at least one determined spectral marker (preferably from the value of at least the three determined spectral markers) which corresponds to at least one absorption spectrum identified for the product.

Thus, and as mentioned above, the method consists of taking the absorption spectra for samples of the first pure compound and for samples of the second pure compound. Additionally, the method may, then, consist of identifying the absorption spectra for the chemical compounds near the first and second compounds. Such chemical compositions can be constituted by synthetic mixtures containing, as the case may be, the first compound or the second compound, as well as another heavier or lighter product.

Figure 2:
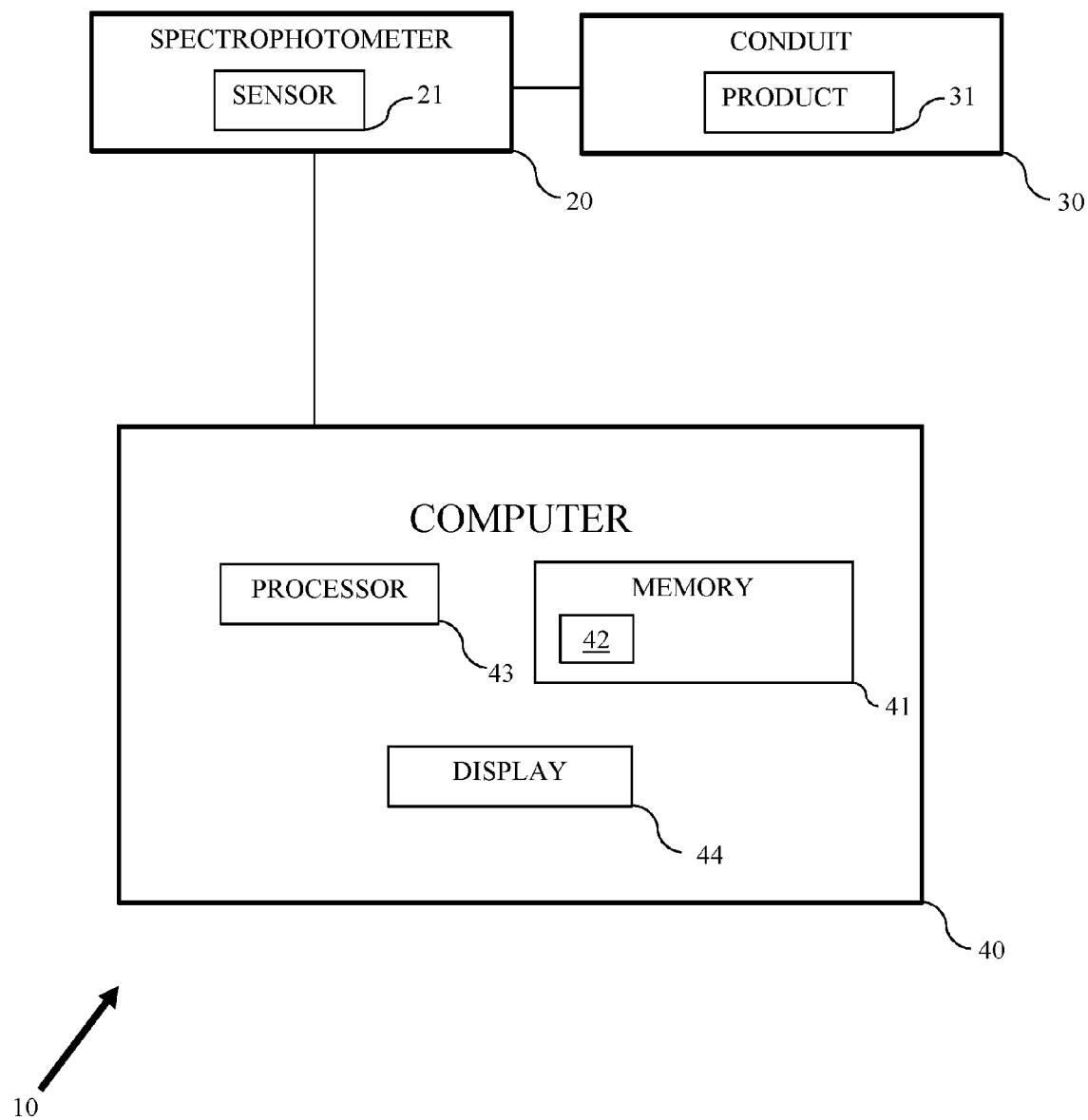
FIG. 2 is a schematic showing one system for characterizing a product in accordance with the present invention.

The method also consists in identifying at least the absorption spectrum of the product to be characterized as shown in the characterization of the product of FIG. 1 which can be produced using system 10 of FIG. 2.

In fact, the identification of the absorption spectra (for the first and second compounds, for the near chemical compounds as well as for the product to characterize) is performed using a spectrometer 20.

In a non-restrictive manner, this type of spectrometer 20 may be adapted to perform Raman spectroscopy, NMR, in the field of infrared, UV-visible, or, and preferably near-infrared (NIR).

Such a spectrometer 20 comprises a sensor 21 (fiber type) which, at least to identify a spectrum from the product to be characterized, is introduced inside conduit 30 for conveyance in which the product flows such as product 31.

According to another characteristic of this method, after having identified such an absorption spectrum, the latter is recorded into a database, more specifically, in numeric and/or digital form, e.g., a computer or server 40 having memory 41 storing an electronic database 42.

In fact, such a spectrum may be recorded in this database in crude form and/or after having being submitted to mathematical processing using computer processor 43.

As mentioned above, the characterization method consists in determining at least one spectral marker.

In this regard, it should be noted that, when determining such a spectral marker:
- a plurality of absorbances will be identified which are relevant to the characterization (preferably, in an optimal manner) for the first and second pure compound, from the absorption spectra identified for each sample from a plurality of samples from the first pure compound as well as for each sample of a plurality of samples from the second pure compound;
- one builds at least one spectral marker from a plurality of pertinent absorbances identified;
- at least one such built spectral marker is validated.

More precisely, when a plurality of pertinent absorbances are identified, in fact, one will perform a statistical analysis of the spectra identified for each sample of a plurality of samples from the first pure compound as well as for each sample of a plurality of samples from the second pure compound.

In a preferred embodiment of the invention, one will perform a statistical analysis of absorption spectra by carrying out, either a discriminant factor analysis, or a principal component analysis of these absorption spectra.

The identification of these relevant absorbances then enables building at least one spectral marker, by constructing a function from a plurality of these relevant absorbances.

On this matter, it should be noted that such a function from a plurality of absorbances may be constituted by an absorbance ratio, by a combination (inter alia linear) of absorbances (inter alia standardized), by a ratio of a combination (inter alia linear) of absorbances (inter alia standardized) or the like.

Finally, when a spectral marker is determined, one still ensures a validation of such a spectral marker which was previously built.

In fact, when a spectral marker is validated, one determines whether the first and second compounds are discriminated for at least one such spectral marker, more specifically, for ranges of values of such a spectral label, in the plane of two spectral markers or in the space of at least three spectral markers.

As mentioned above, the method consists in that:
Inside the conduit 30 for conveyance of the product 31, one will conduct, for at least one absorption spectrum for this product flowing inside this conduit,
for at least one such absorption spectrum reading for the product 31 flowing inside the conduit 30, the value of at least one spectral marker is determined which corresponds to at least one predetermined spectral marker for the first and second pure compounds;

However, according to a preferred embodiment of the invention, this method consists of:
inside the conduit for conveyance of the product 31, one will conduct, a series of identifications of an absorption spectrum for this product flowing inside this conduit 30,
for each of the absorption spectra identified for the product flowing inside the conduit 30, the value of at least one spectral marker will be determined which corresponds to at least one predetermined spectral marker for the first and second pure compounds;

This method consists, then, in that it characterizes said product based on function, on the one hand, of the first and second spectral boxes and, on the other hand, on the values of at least one spectral marker determined and corresponding to the absorption spectra identified for the product.

According to another characteristic, this method of characterization of such a product consists, again, of one identifying the spectra corresponding to this product with a determined frequency. The determined frequency is preferably between 1 second and several seconds (chiefly between 10 and 15 seconds).

An additional characteristic of this method consists of this frequency being adjustable, including in the functions of the product's characteristics (more precisely, in that of the product's viscosity) and/or in the product's flow speed within the conduit for conveyance.

Finally, the method according to the invention may, still, consist in that the frequency is changed with which the product's spectra is identified, when, during the characterization of the product by this method, one observes that there is a change in the product's characteristics.

As mentioned above, the invention relates to a method of characterizing a product such as product 31, flowing inside a conduit such as conduit 30, for conveyance of this product, and which may contain a first compound and/or a second compound.

The invention relates, then, also to a method of detecting the transition, between a first compound and a second compound, of a product, which may contain such a first compound and/or such a second compound, and which flows inside a conduit for conveying this product.

In this regard, it should be noted that this detection method is, more specifically, a detection of the transition of the product by implementing the method of characterization described above.

In fact and in such a case, the characterization of this product is more particularly to detect such a transition of this product.

According to a first embodiment, such a method of transition detection consists in that:
the spectral boxes corresponding to at least one spectral marker on a graph are shown which are for the first and second pure compounds;
on the same graph, the value of the determined spectral marker(s) and corresponding to at least one absorption spectrum identified (or corresponding to each spectrum from a succession of identified spectra) for the product flowing within the conduit for conveyance;
for the product, a transition between the first compound and the second compound would be detected, when one observes the value of this (these) spectral marker(s) which are determined and corresponding to this product, moves away from the first spectral box and/or approaches the second spectral box, or corresponds to this second range of values.

In FIG. 1, a preferred embodiment of the invention is illustrated, consisting of a representation of the spectral boxes on a graphic (box "Product A"; box "product B") corresponding on the one hand, to two spectral markers (Kcy; Ksatu) and, on the other hand, to the first and second pure compound, in a plane corresponding to the plane of these two spectral markers (Kcy; Ksatu).

On the same graph (FIG. 1), the values of these spectral markers (Kcy; Ksatu) corresponding to the product, are displayed, again on the same plane of the two spectral markers (Kcy; Ksatu), for a plurality of successive identified absorption spectra of this product (Sample 1 to Sample 5).

In fact, the method consists, more specifically, of ensuring the display of the values of these spectral markers (Kcy; Ksatu), in real time.

In this regard, it is noted that this graphic is, more specifically, displayed on a screen 44 that comprises a device, such as computer 40 of system 10, to implement the method of characterization.

According to a second embodiment of the invention, such a method of detection consists in that one may detect, for the product, the completion of a transition between the first compound and the second compound where, after the value of the spectral marker(s) corresponding to the absorbances identification for a product flowing in a conduit for conveyance which has evolved between the first and second spectral box, the difference between the values of the spectral marker(s) corresponding to at least two consecutive absorption spectra identified for this product is less than or equal to a determined reference point.

In fact, such a determined reference point corresponds, more specifically, to the repeatability of the device to implement the method of characterization.

As mentioned above, the method of characterization (and, consequently, the transition detection method) of such a product consists, again, of one identifying the spectra corresponding to this product with a determined frequency.

In this regard, it should be noted that when the implementation of this method is begun, the method makes it possible to detect a product containing a first compound. When the second compound arrives in the conduit for conveyance, the method makes it possible to detect a transition of this product between the first compound and the second compound. During such a transition, the spectra vary in each identification, as a function of the dilution of the second compound in the first compound and vice versa. This method also allows, then, the detection of completion of such a transition (the item in the conduit for conveyance is then constituted by the second pure compound) where, as mentioned above, the difference between the values of the spectral marker(s) corresponding to at least two successive absorption spectra identified for this product is less than or equal to a predetermined reference point.

By knowing the identification frequency of the spectra, it is then, possible to determine the precise moment (instant) that the transition is complete, i.e., the precise instant where the second compound replaces the first compound and where the conduit for conveyance no longer contains the second pure compound.

This method allows, then, to validate the composition of the product and thus to take the necessary measures for the further evolution of this material (e.g., validate its loading, transport, or other).

In this way, this method also makes it possible to maximize the quantity of non-degraded product during the transition.

As mentioned above, the invention relates to a method of characterizing a product flowing inside a conduit for conveyance of this product, and which may contain a first compound and/or a second compound.

This invention also relates then, to a method for determining the composition of a product, flowing within a conduit for conveying this product, and which may contain a first compound and/or a second compound.

In this regard, it should be noted that this product composition detection method is, more specifically, a way to determine this composition by implementing the method of characterization described above.

In fact and in such a case, the characterization of this product is more particularly to determine the composition of this product.

This method to determine composition is, specifically, one that determines the product composition by calculating the rate (more specifically, the percentage, inter alia the volume percentage) of the first compound and/or of the second compound on the inside of this product, based on, firstly, the first and second spectral boxes of at least one spectral marker and, secondly, on the value of at least one spectral marker of the product and corresponding to the absorption spectra identified for the product.

Specifically, this method makes it possible to determine the composition of a product constituted by a mixture of the first and second compounds, with great accuracy.

This method also makes it possible to follow the evolution of this mixture over time.

Finally, this method to determine the composition of a product makes it possible, advantageously, to verify and monitor the transition of this product between a first compound and a second compound, during the flow of this product within a conduit for conveyance.

As mentioned above, this invention relates to a method of characterizing a product flowing inside a conduit for conveyance of this product, and which may contain a first compound and/or a second compound.

This invention also relates then, to a method characterizing a product, flowing within a conduit for conveying this product, and which may contain a first compound and/or a second compound.

More specifically, this device is designed to implement the method of characterization described above.

This device comprises, then, a database containing at least the absorption spectra from a plurality of samples from the first pure compound and from a plurality of samples from the second pure compound;

Additionally, this database may then, consist of absorption spectra for the chemical compounds near the first and second compounds. Such chemical compositions can be constituted by synthetic mixtures containing, as the case may be, the first compound or the second compound, as well as another heavier or lighter product.

In fact, this database, e.g., database 42 can include such absorption spectra, especially in digital and/or digitized form, stored in this database 42.

In this regard, it should be noted that such a spectrum may be recorded in this database in crude form and/or after having being submitted to mathematical processing.

Additionally, this database may then, consist of information regarding physical and/or chemical properties of the first and second compounds.

In fact, such a database 42 is incorporated into a computer 40 (specifically in memory 41 that comprises such a computer) that includes the characterization device according to the invention.

The characterization device, such as system 10, comprises, then, the means to determine at least one spectral marker, common to the first compound and to the second compound (e.g., spectrometer 20), discriminating thus discriminating the first and second components, and consisting of a function of a plurality of absorbances from such spectrum using processor 43.

From these means to determine at least one spectral marker comprising the means to identify a plurality of pertinent absorbances which make it possible to characterize (preferably in an optimal manner) for the first and second pure compounds, from this absorption spectra identified for each sample from each sample from a plurality of samples from the first pure compound as well as for each sample of a plurality of samples from the second pure compound.

Indeed, such means of identification are constituted by the means for statistical analysis of the spectra identified for each sample from a first plurality of samples from the first pure compound as well as for each sample of a plurality of samples from the second pure compound;

Such means of statistical analysis of absorption spectra are designed to perform, either a discriminant factor analysis, or a principal component analysis of the absorption spectra.

Such means for determining at least one spectral marker include, again, the means to build at least one spectral marker from a plurality of pertinent absorbances identified.

These means to build are designed to build at least one spectral marker constituted by a function of a plurality of these pertinent identified absorbances. This type of function may be constituted by an absorbance ratio, by a combination (inter alia linear) of absorbances (inter alia standardized), by a combination ratio (inter alia linear) of absorbances (inter alia standardized) or the like.

Such means for determining at least one spectral marker include, again, the means to validate at least one pre-built spectral marker. Such means for validation are designed to determine whether the first and second compounds are discriminated, as appropriate, for such a spectral marker, in the plane of two spectral markers or in the space of at least three spectral markers.

In fact, the means for statistical analysis, the means for building at least one spectral marker, and the means for validating at least one such spectral marker, are constituted by a software operating on-a the computer 40 comprising the characterization device (e.g., system 10) according to the invention.

The characterization device comprises, then, the means to define, on the one hand, a first spectral box constituted by a first spectral range delimited by the values of at least one such spectral marker determined and corresponding to the first pure compound and, on the other hand, a second spectral box constituted by a second spectral range delimited by the values of at least one such spectral marker determined and corresponding to the second pure compound, for at least one predetermined spectral marker.

Again, the means for determining such a spectral box is constituted by a software operating on a computer comprising the characterization device according to the invention.

This characterization device also comprises, the means to identify, on the inside the conduit for conveyance of the product, at least one absorption spectrum for this product flowing inside this conduit, or a succession of absorption spectra for this product flowing inside this conduit.

Such means for identification comprises a spectrometer such as spectrometer 20 (Raman, NMR, infrared, UV-visible, and preferably near-infrared (NIR) type) on the one hand, it comprises a probe (including the fiber type, inserted into the conduit for conveyance), and, on the other hand, it comprises the characterization device of the invention.

Moreover, this device comprises the means for determining the value of at least one spectral marker corresponding to at least one predetermined spectral marker for the first and second pure compounds, for at least one identified absorption spectrum for the product flowing inside the conduit, or for each of the absorption spectra corresponding to a succession of absorption spectra identified for this product flowing inside this conduit.

Such means are then, so designed as to calculate a value, on the one hand, from at least one absorption spectrum (respectively from each of the spectra of a succession of spectra) identified for this product flowing inside this conduit. on the other hand, by applying at least one function, constituting at least one spectral marker, to a plurality of relevant absorbances of one such spectrum (respectively of each of the spectrums) and identified for this product.

Finally, the characterization device comprises the means to characterize said product, based on, firstly, the first and second spectral boxes and, secondly, on the value of at least one spectral marker determined and corresponding to at least one absorption spectrum identified for the product.

The invention also relates to a device to detect the transition between a first compound and a second compound, of a product, which may contain such a first compound and/or such a second compound, and which flows inside a conduit for conveying this product.

This detection device for the transition is constituted by a characterization device presenting the characteristics described above and in which, according to a first embodiment, the means to characterize a product comprising:

the spectral boxes corresponding to at least one spectral marker on a graph are shown which are for the first and second pure compounds;

a means to display, on the same graph, the value of the determined spectral marker(s) and corresponding to at least one absorption spectrum identified (or to a plurality of identified absorption spectra) for the product flowing within the conduit for conveyance.

For such a device, a transition between the first compound and the second compound is detected for the product when viewed, on said graph, or the value of the spectral markers determined and corresponding to this product which moves away from the first spectral box and/or it approaches the second spectral box or it corresponds to the second spectral box.

This type of graphic is displayed on a screen that comprises the characterization device according to the invention.

According to a second embodiment, the means to characterize a product comprises:

a means to calculate the difference between the values of the spectral marker(s) corresponding to at least two successive absorption spectra identified for this product;

a means to compare this difference to a determined reference point (corresponding more specifically to the repeatability of the device);

a means to detect, for the product, the completion of a transition between the first compound and the second compound when this difference is less than or equal to the value of the reference point.

This invention relates, then, to a device for determining the composition of a product, flowing within a conduit for conveying this product, and which may contain a first compound and/or a second compound.

This device to determine the composition is constituted by a characterization device presenting the characteristics described above and in which the means to characterize a product comprising a means to calculate the rate (more specifically, the percentage, including the volume) of the first compound and/or of the second compound on the inside of this product, based on, firstly, the first and second spectral boxes of at least one spectral marker and, secondly, on the value of at least one spectral marker of the product and corresponding to the absorption spectra identified for the product.

Again, the means for characterizing said product is constituted by software operating on a computer comprising the characterization device according to the invention.

The invention claimed is:

1. A method of detecting the transition, between a first compound and a second compound, of a product, said method comprising:
    detecting an absorption spectrum for each sample using a spectrometer from a first plurality of samples from the first pure compound as well as for each sample of a plurality of samples from the second pure compound;
    identifying from the absorption spectra using a computer processor, at least one spectral marker, which is common to the first and second compounds, to thereby allow discrimination between the first and second compounds, and consisting of a function of a plurality of absorbances from such a spectrum;
    identifying at least one predetermined spectral marker, using a computer processor, from each of the absorption spectra for:
        (i) a first spectral box constituted by a first spectral range delimited by the values of at least one such spectral marker determined and corresponding to the first pure compound and
        (ii) a second spectral box constituted by a second spectral range delimited by the values of at least one such spectral marker determined and corresponding to the second pure compound;
    identifying at least one absorption spectrum of the product flowing inside the conduit for conveyance of the product;
    identifying the value of at least one predetermined spectral marker for the first and second pure compounds, using a computer processor, based on at least one such absorption spectrum identified for the product flowing inside the conduit; and
    identifying the product flowing through the conduit a transition between the first and second compound, using a computer processor, when the value of the determined spectral marker(s) corresponding to at least one absorption spectrum identified for the product flowing within the conduit for conveyance, moves away from the first spectral box and/or approaches the second spectral box, or corresponds to this second spectral box.

2. The method of detection of the transition of a product according to claim 1, wherein:
    identifying from the absorption spectra at least one spectral marker comprises identifying two spectral markers, which are common to the first and second compounds to thereby allow the discrimination between the first and second compounds, and each of the spectral markers consisting of a function of a plurality of absorbances from such a spectrum;
    from the absorption spectra identified for the samples from the first and second pure compound, the identifying the first spectral box is defined constituted by a first spectral range delimited by the values of these two spectral markers determined and corresponding to the first pure compound and, identifying the second spectral box is constituted by a second spectral range delimited by the values of these two spectral markers determined and corresponding to the second pure compound, for at least the two predetermined spectral markers and in a space corresponding to these two spectral markers; and
    the identifying the value of at least one predetermined spectral marker comprises identifying two spectral markers corresponding to the predetermined two spectral markers for the first and second pure compounds.

3. A method of detection of the transition of a product according to claim 1, wherein:
    identifying at least one absorption spectrum of the product flowing inside the conduit for conveyance of the product; comprises identifying a succession of identifications of an absorption spectrum of the product flowing inside this conduit; and
    identifying the value of at least one predetermined spectral marker for the first and second pure compounds is performed for each of the absorption spectrum identified for the product flowing inside the conduit.

4. The method of detection of the transition of a product according to claim 3, wherein completion of a transition may be detected in the product between the first compound and the second compound when, after the value of the spectral marker(s) corresponding to the absorption spectra identified for a product flowing in a conduit for conveyance which has evolved between the first and second spectral box, the difference between the values of the spectral marker(s) corresponding to at least two successive absorption spectra identified for this product is lower or equal to a determined reference point.

5. The method of detection of the transition of a product according to claim 1, characterized by the fact that the absorption spectra are identified by Raman spectroscopy, NMR, in the field of infrared, visible-UV, or near infrared.

6. The method of detection of the transition of a product according to claim 1, wherein, when at least one spectral marker is determined:
    a plurality of relevant absorbances are identified to characterize the first and second pure compounds, from the absorption spectra identified for each sample of a plurality of samples from the first pure compound as well as for each sample of a plurality of samples from the second pure compound; and
    further comprising building at least one spectral marker from a plurality of relevant absorbances identified, wherein at least one such spectral marker is validated.

7. The method of detection of the transition of a product according to claim 6, wherein, when a plurality of relevant absorbances has been identified, the method further comprises applying statistical analysis to the spectra identified for each sample from each sample from a plurality of samples from the first pure compound as well as for each sample of a plurality of samples from the second pure compound.

8. The method of detection of the transition of a product according to claim 6, wherein from the relevant absorbances identified, at least one spectral marker is built by building a function from a plurality of these relevant absorbances constituted by an absorption ratio by a combination of absorbances, by a ratio of combinations of absorbances.

9. The method of detection of the transition of a product according to claim 6, wherein, when at least one spectral marker is validated, identifying whether the first and second compounds are discriminated for at least one such spectral marker.

10. A device for the detection of the transition of a product, flowing inside a conduit for conveyance of this product, the device comprising:
an electronic database stored in computer memory containing at least the absorption spectra from a plurality of samples from the first pure compound and from a plurality of samples from the second pure compound;
a spectrometer with sensor, the spectrometer adapted to identify at least one spectral marker, common to the first compound and to the second compound, to thereby allow discrimination between the first and second compound, and consisting of a function of an absorbance plurality from this spectrum, the spectrometer adapted to identify, on the inside of the conduit for conveyance of the product, at least one absorption spectrum for this product flowing inside this conduit;
a computer executing non-transiting software instruction, said instruction comprising:
identifying a first spectral box constituted by a first spectral range delimited by the values of at least one such spectral marker identifiable by the spectrophotometer and corresponding to the first pure compound and a second spectral box consists of a second range of values of the spectral marker delimited by the values of at least one such spectral marker determined and corresponding to the second pure compound, for at least one predetermined spectral marker;
identifying the value of at least one spectral marker, corresponding to at least one predetermined spectral marker for the first and second pure compounds, for at least one absorption spectrum identified for the product flowing inside the conduit; and
characterizing the product based on the first and second spectral boxes and from the value of at least one spectral marker determined and corresponding to at least one absorption spectrum identified for the product.

11. The device according to claim 10, wherein characterizing the product via software instruction comprises:
calculating a difference between the values of the spectral marker(s) corresponding to at least two successive absorption spectra identified for this product;
comparing the difference to a determined reference point; and
identifying, for the product, a completion of a transition between the first compound and the second compound when this difference is less than or equal to this reference value.

12. The device for the detection of the transition of a product according to claim 10, wherein the spectrometer with sensor is adapted to permit identification of a plurality of relevant absorbances to make it possible to characterize the first and second pure compounds and to build at least one spectral marker from a plurality of relevant absorbances and constituted by a function of a plurality of these relevant absorbances identified.

13. The device for the detection of the transition of a product according to claim 10, wherein the spectrometer is selected from the group consisting of a Raman, NMR, in the field of infrared, visible-UV, and near-infrared type.

14. The device of claim 13, wherein the sensor comprises a probe inserted into the conduit for conveyance.

15. The device of claim 10, further comprising a display operatively associated with the computer to display the spectral boxes and the value of the identified spectral marker(s) and corresponding to at least one absorption spectrum identified for the product flowing within the conduit on a single graph.

* * * * *